United States Patent [19]

Ueda

[11] Patent Number: 4,810,609
[45] Date of Patent: Mar. 7, 1989

[54] PHOTOSENSITIVE MEMBER WITH ENAMINE CHARGE TRANSPORT MATERIAL

[75] Inventor: Hideaki Ueda, Kawanishi, Japan

[73] Assignee: Minolta Camera Kabushiki Kaisha, Osaka, Japan

[21] Appl. No.: 35,185

[22] Filed: Apr. 7, 1987

[30] Foreign Application Priority Data

| | | |
|---|---|---|
| Apr. 8, 1986 [JP] | Japan | 61-80780 |
| Apr. 16, 1986 [JP] | Japan | 61-88491 |
| May 12, 1986 [JP] | Japan | 61-108052 |
| May 12, 1986 [JP] | Japan | 61-108053 |
| May 20, 1986 [JP] | Japan | 61-115918 |

[51] Int. Cl.⁴ .............................. G03G 5/09
[52] U.S. Cl. .......................... 430/83; 430/59; 430/81; 430/96; 430/95
[58] Field of Search ............. 430/59, 81, 83, 90, 430/95

[56] References Cited

U.S. PATENT DOCUMENTS 4,334,001  6/1982  Horie et al. ................. 430/81 X

FOREIGN PATENT DOCUMENTS 48-28299  8/1973  Japan ....................... 430/83
59-165064  9/1984  Japan ....................... 430/59

Primary Examiner—Roland E. Martin
Attorney, Agent, or Firm—Burns, Doane, Swecker & Mathis

[57] ABSTRACT

The present invention provides a photosensitive member having a charge transporting layer containing a new enamine compound which has a specific substituent on the terminal carbon of the enamine bone, which give an excellent charge transportability.

20 Claims, 1 Drawing Sheet

PHOTOSENSITIVE MEMBER WITH ENAMINE CHARGE TRANSPORT MATERIAL

BACKGROUND OF THE INVENTION

In the electrophotographic art, the following methods are commonly known: the direct method, wherein the surface of a photosensitive layer of a photosensitive member is given a charge and subjected to an exposure to form a latent electrostatic image which is developed with a developer to visualize the image, thereupon the visualized image is directly fixed on the photosensitive member in order to provide a copied image; the toner image transfer method, wherein a visual image on a photosensitive member is transferred onto a transfer paper, made of a paper, for example, where the transferred image is fixed to form a copied image; the latent image transfer method, wherein a latent electrostatic image on a photosensitive member is transferred onto a transfer paper where the latent electrostatic image is developed and fixed.

It is conventionally known that inorganic photoconductive materials, such as selenium, cadmium sulfate, zinc oxide and the like, are used as photoconductive materials to form the photosensitive layer of a photosensitive member employed in the electrophotographic methods, mentioned above. These photoconductive materials have diverse advantages; they can be given electrical charge of a proper potential; the smaller effluence of charge in the dark, and the irradiation to light can raidly neutralize the charge. Such materials, however, have various disadvantages. For example, selenium photosensitive materials incur greater manufacturing costs and require careful handling, since they are vulnerable to heat and mechanical impacts. Cadmium sulfate photosensitive members and zinc oxide photosensitive members cannot provide either stable sensitivity under the highly humid environment or stable properties for a long period because a coloring material incorporated into the members causes both charge-oriented deterioration due to corona charge and colorfading due to exposure.

On the other hand, various organic photoconductive polymers including polyvinyl carbazole have already been proposed. Compared to the above-mentioned inorganic photoconductive materials, these polymers excel in properties including coating properties, lightness, but are inferior in sensitivity, durability, and stability to environmental fluctuation.

Low molecule organic photoconductive compounds are preferable since their coating properties or electrophotographic properties can be regulated by arbitrarily designating the type, composition and the like, of a binder being used together with the compounds. However, the combined use with a binder requires that each of the compounds is highly compatible with the binder.

The photosensitive member containing high molecular or low molecular weight organic photoconductive compounds being dispersed into the resin or binder have disadvantages including a greater residual potential due to the greater number of traps in the carrier which causes poor sensitivity. Accordingly, there have been proposals for blending a charge transporting material with an organic photoconductive compound in order to solve the above-mentioned disadvantages.

Diverse organic compounds have been disclosed as charge transporting materials, however, these compounds have various disadvantages. 2,5-bis(P-diethylaminophenyl)-1,3,4-oxadiazoles, for example, described in U.S. Pat. No. 3,189,447, have a poor compatibility with a binder, and tend to crystallize. Diarylalkane derivatives described in U.S. Pat. No. 3,820,989, though having satisfactory compatibility with a binder, develop deterioration in sensitivity due to repeated use. Hydrazon compounds described in Japanese Patent Publication Laid Open to Public Inspection No. 59143/1979, though having comparatively good residual potential properties, are disadvantageously inferior in sensitivity and charging capacity.

Thus, it is the fact that there are few charge transporting materials having properties practically advantageous in forming a photosensitive member.

SUMMARY OF THE INVENTION

The present invention provides a photosensitive member containing an enamine compound as a charge transporting material. The photosensitive member of the invention excels in the charge transporting properties, has a stable initial surface potential, and features a satisfactory charging capacity. With its charge transporting properties being remarkably excellent, and which fewer traps in the carrier, a photosensitive member having much higher sensitivity than that obtainable from a conventional charge transporting material can be provided.

BRIEF DESCRIPTION OF DRAWINGS

FIGS. 1, 4 and 5 respectively illustrate the structure of a dispersion type photosensitive member comprising an electroconductive substrate, provided thereon, a photosensitive layer.

FIGS. 2 and 3 respectively illustrate the structure of a function separating type photosensitive member comprising an electroconductive substrate, provided thereon, a charge generating layer and a charge transporting layer.

DETAILED DESCRIPTION OF THE INVENTION

Figure 1:
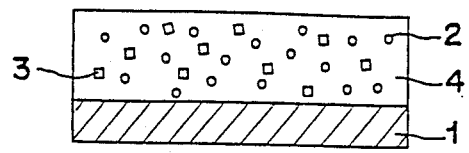
FIGS. 1 through 5 are schematic representations of photosensitive members according to the invention.

The present invention relates to a photosensitive member having a photosensitive layer containing an enamine compound expressed by the following general formula (I) as a charge transporting material:

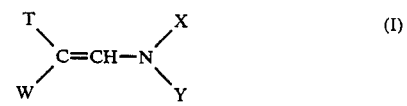

wherein T and W are independently hydrogen, halogen, alkyl group, or alkoxyaryl group, aralkyl group, alkyl group, di-substituted aminoaryl group, alkylaryl group, halogenized aryl group,

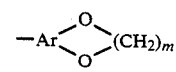

(Ar is aryl group and m is 1 or 2), heterocyclic group or a condensed polycyclic group, each of which may have one or more another substituents, providing that at least one of T and W is an alkyl group, di-substituted aminoaryl group, alkylaryl group, halogenized aryl group,

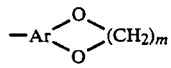

(Ar is an aryl group and m is 1 or 2), heterocyclic group or condensed polycyclic group, each of which may have one or more other substituents, and X and Y are independently hydrogen, alkyl group, or phenyl group, alkoxyaryl group or aralkyl group, each of which may have one or more substituents excepting alkyl and/or di-substituted amino group, except that both the X and Y are not hydrogen.

The characteristic of the photosensitive member of the present invention is that the emanime compound having a specific substituent on a carbon atom of the emanine bone is used in the charge transporting layer of the photosensitive member. The obtained photosensitive member excels in the charge transporting properties, has a stable initial surface potential, and features a satisfactory charging capacity.

In the above formula (I) T and W are independently hydrogen, halogen, alkyl group, or alkoxyaryl group, aralkyl group, di-substituted aminoaryl group, alkylaryl group, halogenized aryl group,

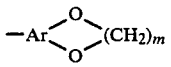

(Ar is an aryl group and m is 1 or 2), heterocyclic group or condensed polycyclic group, each of which may have one or more other substituents, providing that at least one of T and W is an alkyl group, di-substituted aminoaryl group, alkylaryl group, halogenized aryl group,

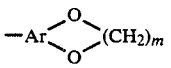

(Ar is an aryl group and m is 1 or 2), heterocyclic group or condensed polycyclic group, each of which may have one or more another substituents. X and Y are independently hydrogen, alkyl group, or phenyl group, alkoxyaryl group or aralkyl group, each of which may have one or more substituents excepting alkyl and/or di-substituted amino group, excepting that both the X and Y are hydrogen.

The alkyl group may be linear, branched, saturated, or unsaturated, and preferably saturated hydrocarbons having one to four carbon atoms (referred to as $C_1$-$C_4$ alkyl group).

As the haogen chlorine or fluorine is preferable.

As the alkoxyaryl group an aryl group having one or more $C_1$-$C_3$ alkoxy group(s) is preferable, and the aryl group includes phenyl, naphthyl and anthryl. Most preferable one is a $C_1$-$C_3$ alkoxyphenyl group. These aryl groups may have another substituent such as alkyl group, halogen and the like.

As the aralkyl group benzyl group which may have one or more substituents such as halogen, alkyl group, di-substituted amino group, dioxaalkylene, group alkoxy group and the like.

As the di-substituted aminoaryl group, an aryl group such as phenyl, naphthyl, anthryl and the like having a (di-$C_1$-$C_4$ alkyl)amino group, morpholinyl group, piperidyl group, piperazinyl group, 2,3-dihydropyridyl group or tetrahydroquinolyl group.

The halogenized aryl group is preferably a chlorophenyl or fluorophenyl group.

The heterocyclic group is preferably a pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group.

The condensed polycyclic group is preferably a naphthyl group, alkoxy group, di-substituted aminonaphthyl group or anthryl group.

In the group represented by

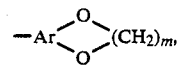

Ar may be a phenyl, naphthyl, anthryl and the like, which may have substituents such as an alkyl group, halogen and so on, and m is preferably an integer of 1 or 2.

If the T and/or W is a halogenized phenyl group, X and/or Y is preferably a phenyl group or alkoxyphenyl group.

If the T and/or W is a di-substituted aminoaryl group, the X and/or Y is preferably a phenyl group, alkoxyphenyl group or benzyl group.

If the T and/or W is a heterocyclic group, the X and/or Y is preferably a phenyl group or alkoxyphenyl group.

If the T and/or W is a group represented by the formula:

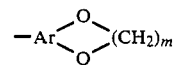

(m is 1 or 2) X and/or W is preferably a phenyl group, alkoxyphenyl group or benzyl group.

If the T and/or W is a condensed polycyclic group, the X and/or Y is preferably a phenyl group or an alkoxyphenyl group.

When T and W have any of the above-mentioned substituents, the photosensitive member can excel in electrophotographic properties including photosensitivity, residual potential, photo-fatigue and others, each of which being stable for a longer period.

The enamine compounds, according to the invention, represented by the general formula (I) are preferably those expressed by the following formulas (I-1)-(I-9). However, it should be noted that the scope of the invention is not limited only to these compounds.

The examples of the enamine compounds, mentioned above, used in the invention include those represented by the following general formula:

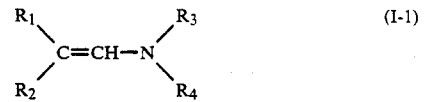

wherein, $R_1$ and $R_2$ are independently hydrogen, halogen, alkyl group, or alkoxyaryl group, aralkyl group, alkyl group, di-substituted aminoaryl group, alkylaryl group, halogenized aryl group,

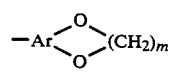

(Ar is an aryl group, and m is 1 or 2), heterocyclic group or condenced polycyclic group, each of which may have one or more other substituents, providing that at least one of $R_1$ and $R_2$ are an aminoaryl group which have alkyl groups, morpholinyl group, piperidyl group, piperazinyl group, 2,3-dihydropyridyl group or tetrahydroquinolyl group and aryl group is a phenyl, naphthyl or anthryl group; $R_3$ and $R_4$ are independently hydrogen, alkyl group, or phenyl group, alkoxyaryl group or aralkyl group, each of which may have one or more substituents excepting alkyl and/or di-substituted amino group, except that both the $R_3$ and $R_4$ are not hydrogen. The $R_3$ and/or $R_4$ is preferably a phenyl group, alkoxyphenyl group or benzyl group.

The typical examples of these enamine compounds include those having one of the following structures.

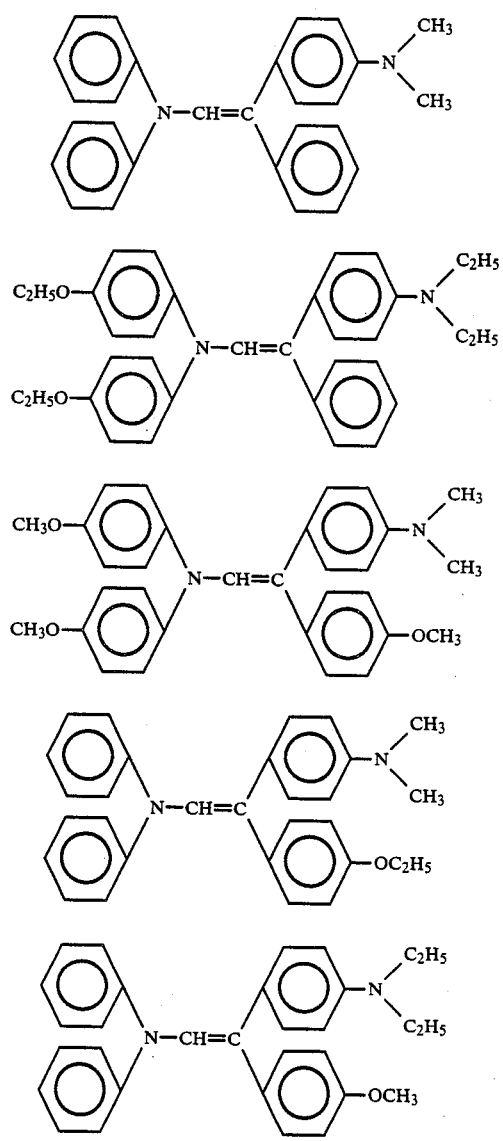

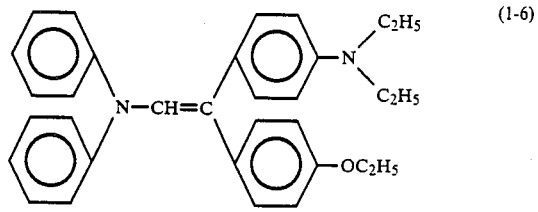

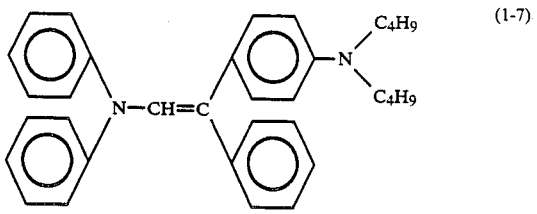

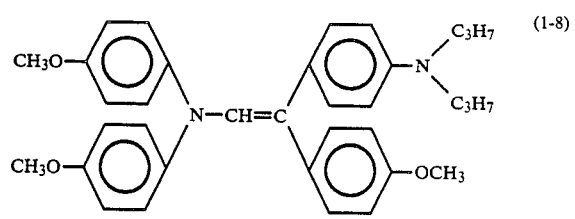

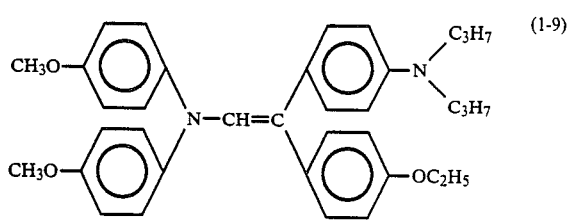

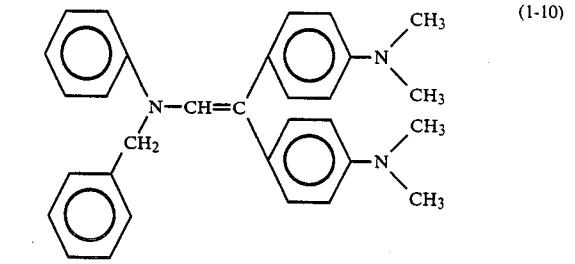

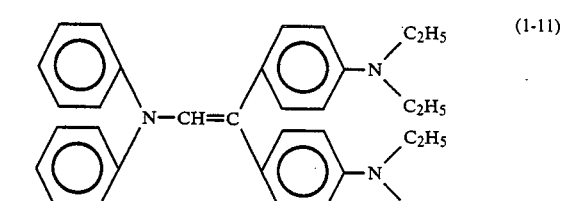

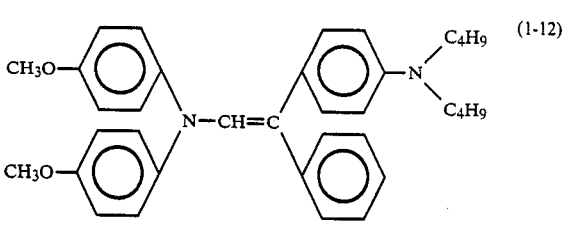

-continued

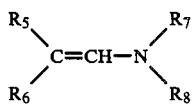

Still other enamine compounds usable for the invention are those expressed by the following general formula:

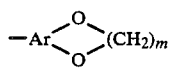
(I-2)

wherein $R_5$ and $R_6$ are independently hydrogen, halogen, alkyl group, or alkoxyaryl group, aralkyl group, alkyl group, di-substituted aminoaryl group, alkylaryl group, halogenized aryl group, $$-Ar\underset{O}{\overset{O}{\diagup\hspace{-0.5em}\diagdown}}(CH_2)_m$$

(Ar is an aryl group, and m is 1 or 2), heterocyclic group or condensed polycyclic group, each of which may have one or more another substituents, providing that at least one of $R_5$ and $R_6$ are an heterocyclic group selected from the group consisting of a pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group; and $R_7$ and $R_8$ are independently hydrogen, alkyl group, or phenyl group, alkoxyaryl group or aralkyl group, each of which may have one or more substituents except an alkyl and/or di-substituted amino group, except that both the $R_7$ and $R_8$ are not hydrogen. The $R_5$ and/or $R_6$ is most preferably a phenyl group or alkoxyphenyl group.

The typical examples of an enamine compound according to the invention expressed by general formula (I-2) include those having the following structures. However, it should be noted that the scope of the invention is not limited only to these examples.

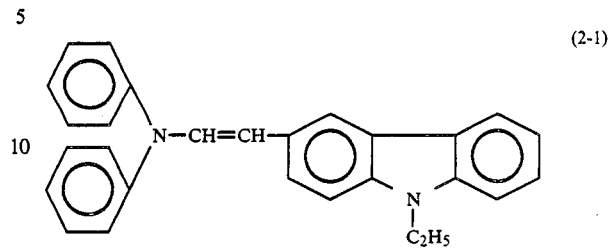

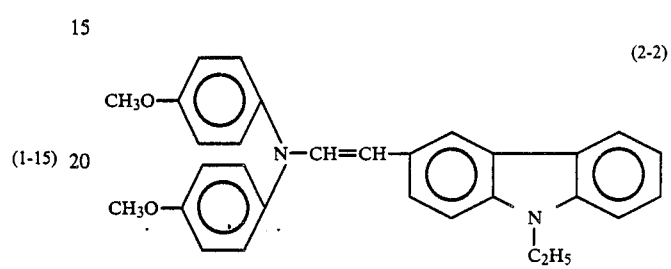

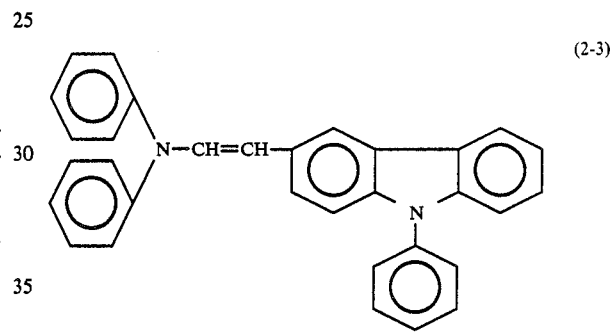

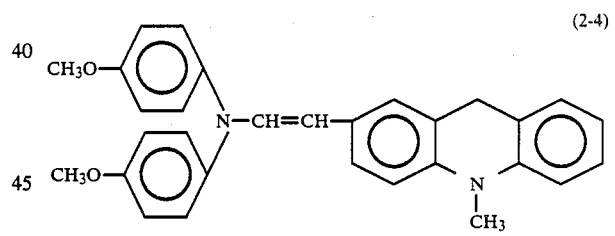

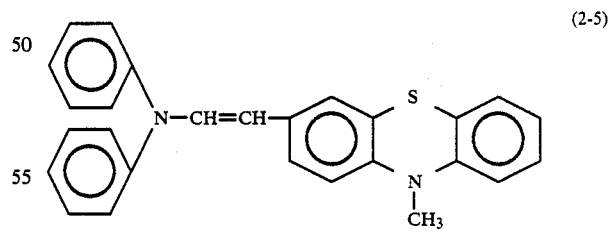

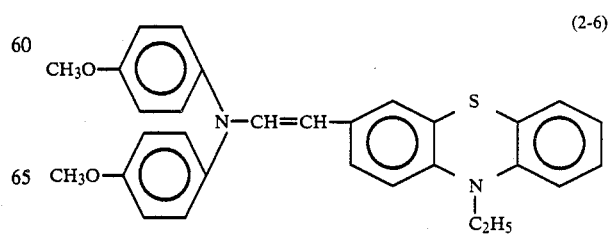

(2-7) 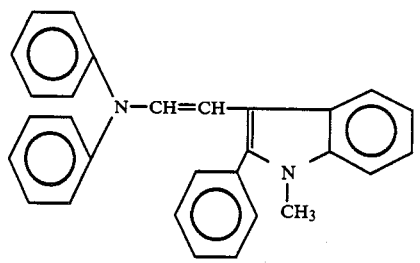
(2-8) 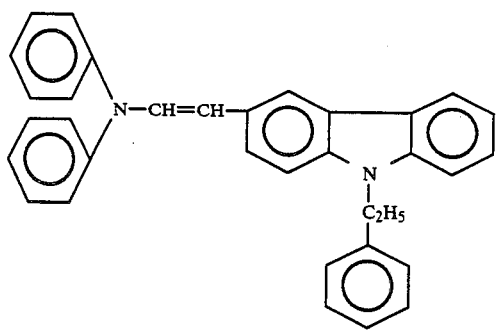
(2-9) 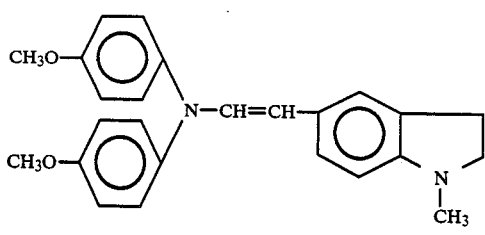
(2-10) 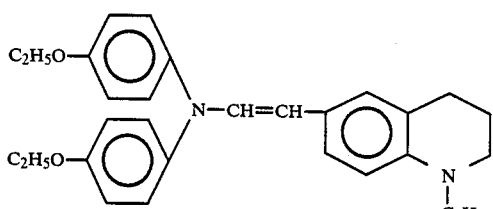
(2-11) 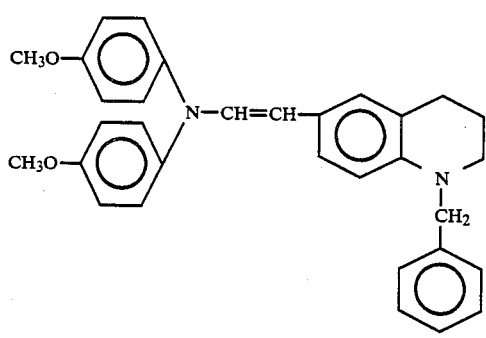
(2-12) 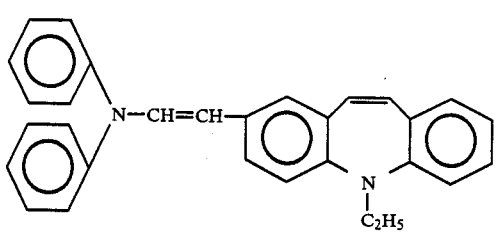
(2-13) 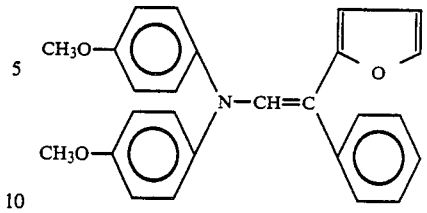
(2-14) 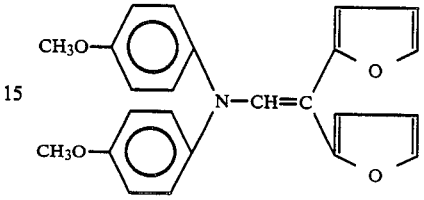
(2-15) 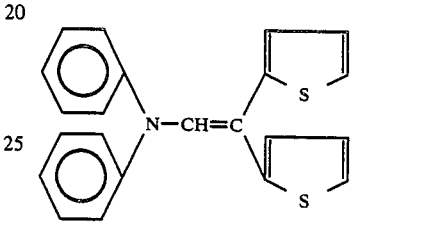
(2-16) 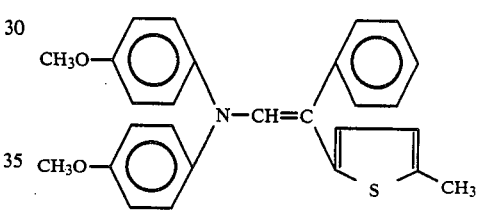
(2-17) 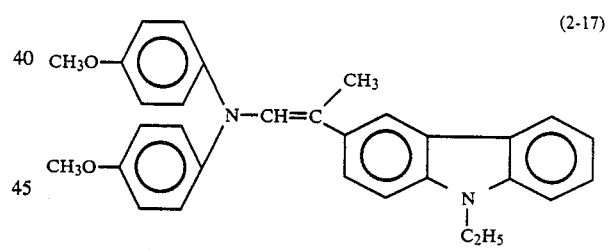
(2-18) 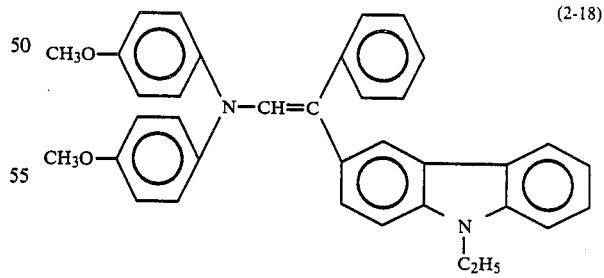
(2-19) 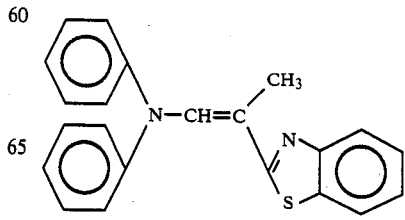

-continued (2-20) 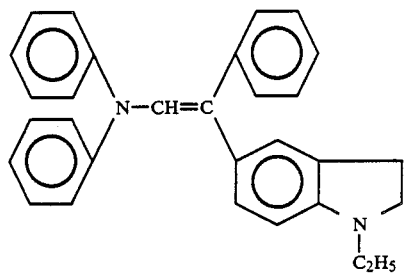

(2-21) 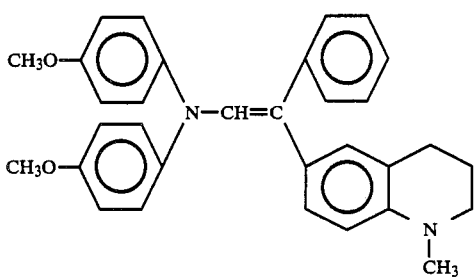

(2-22) 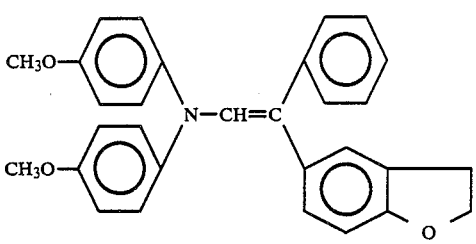

(2-23) 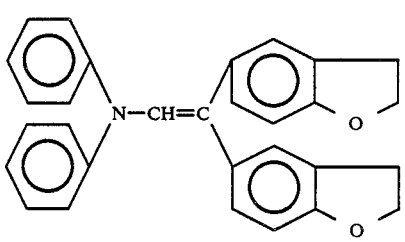

Still other enamine compounds used in the invention are those expressed by the following general formula:

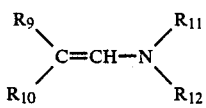
(I-3)

wherein $R_9$ and $R_{10}$ are independently hydrogen, halogen, alkyl group, or alkoxyaryl group, aralkyl group, alkyl group, di-substituted aminoaryl group, alkylaryl group, halogenized aryl group,

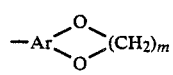

(Ar is an aryl group and m is 1 or 2), heterocyclic group or condensed polycyclic group, each of which may have one or more other substituents, providing that at least one of $R_9$ and $R_{10}$ are a group of

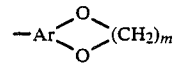

(m is 1 or 2, and Ar is an aryl group) and $R_{11}$ and $R_{12}$ are independently hydrogen, alkyl group, or phenyl group, alkoxyaryl group or aralkyl group, each of which may have one or more substituents excepting alkyl and/or di-substituted amino group, except that both the $R_{11}$ and $R_{12}$ are not hydrogen. The $R_{11}$ and/or $R_{12}$ is most preferably an phenyl group, alkoxyphenyl group or benzyl group.

The typical preferred enamine compounds, expressed by (I-3), include those having the following structures.

(3-1) 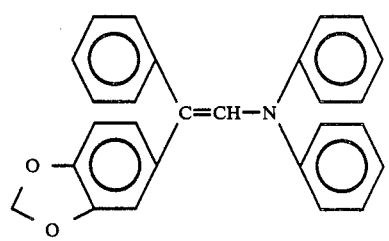

(3-2) 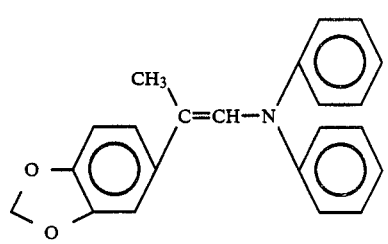

(3-3) 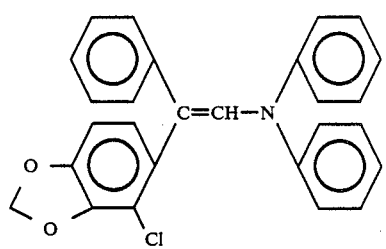

(3-4) 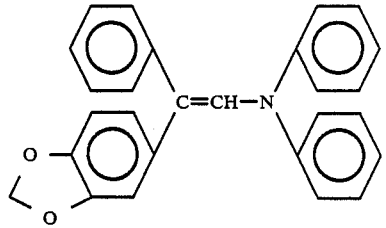

(3-5) 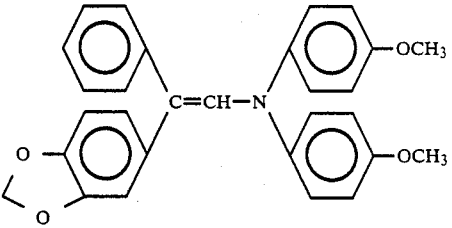

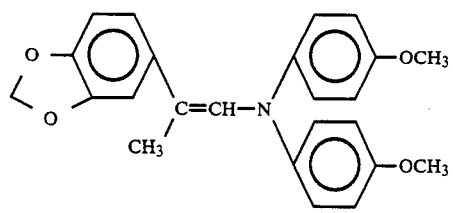
(3-6)
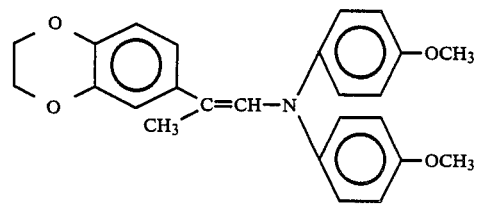
(3-7)
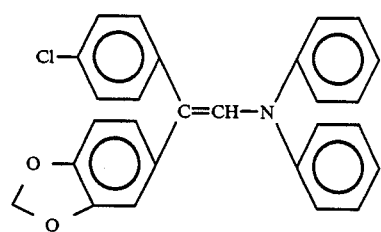
(3-8)
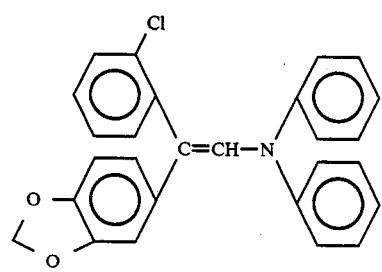
(3-9)
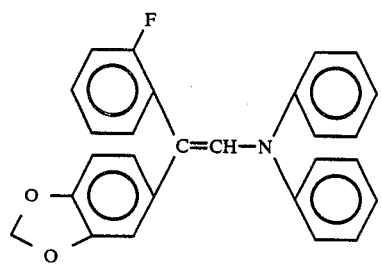
(3-10)
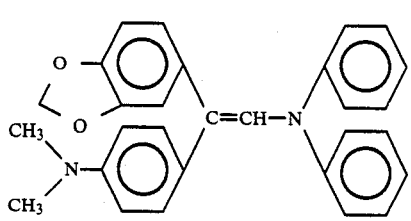
(3-11)
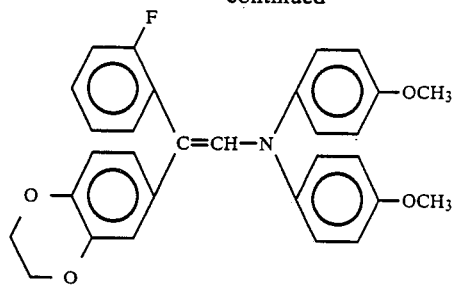
(3-12)
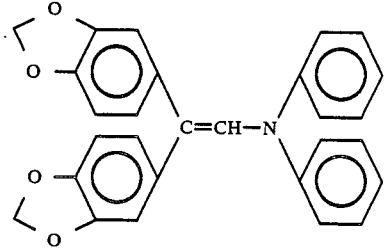
(3-13)
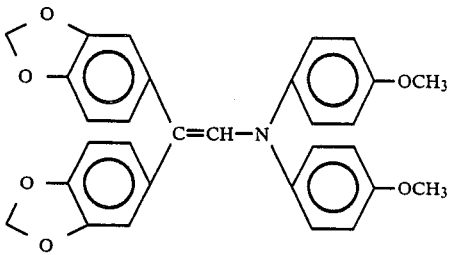
(3-14)
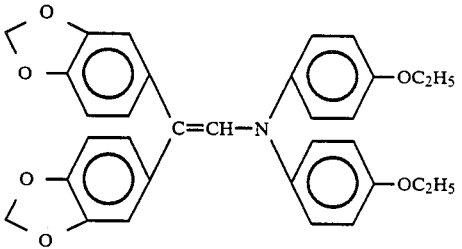
(3-15)
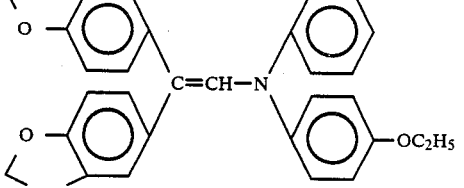
(3-16)
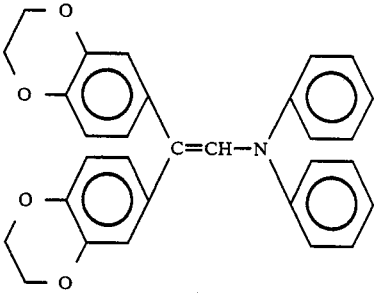
(3-17)

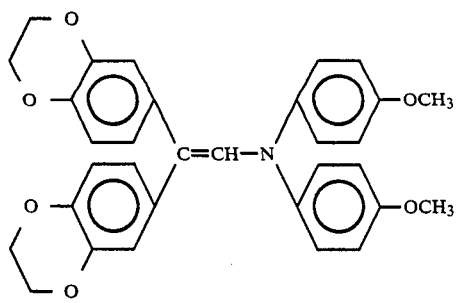
(3-18)

There are still other enamine compounds expressed by the following general formula:

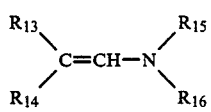
(I-4)

wherein $R_{13}$ and $R_{14}$ are independently hydrogen, halogen, alkyl group, or alkoxyaryl group, aralkyl group, alkyl group, di-substituted aminoaryl group, alkylaryl group, halogenized aryl group,

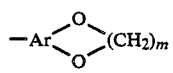

(Ar is an aryl group, and m is 1 or 2), heterocyclic group or condensed polycyclic group, each of which may have one or more other substituents, providing that at least one of $R_{13}$ and $R_{14}$ are an halogenized aryl group; and $R_{15}$ and $R_{16}$ are independently hydrogen, alkyl group, or phenyl group, alkoxyaryl group or aralkyl group, each of which may have one or more substituents excepting alkyl and/or di-substituted amino group, except that both the $R_{15}$ and $R_{16}$ are not hydrogen. $R_{15}$ and/or $R_{16}$ is most preferably a phenyl group or alkoxyphenyl group.

The typical preferred enamine compounds, expressed by (I-4), include those having the following structures.

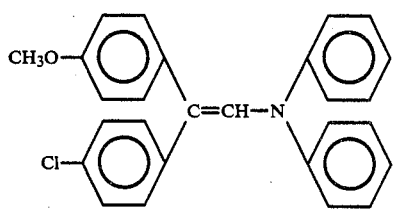
(4-1)

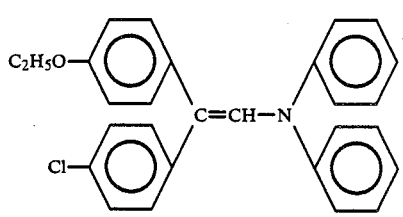
(4-2)

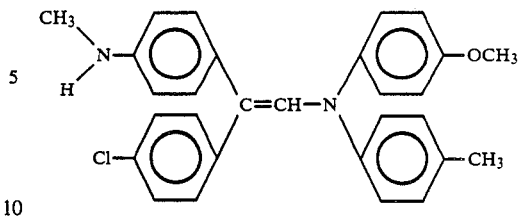
(4-3)

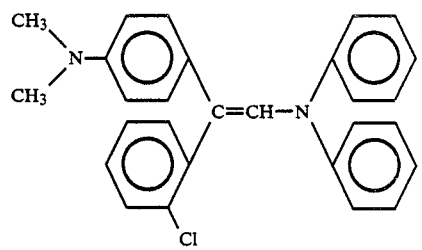
(4-4)

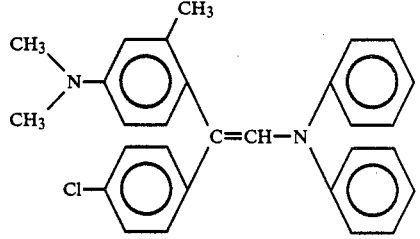
(4-5)

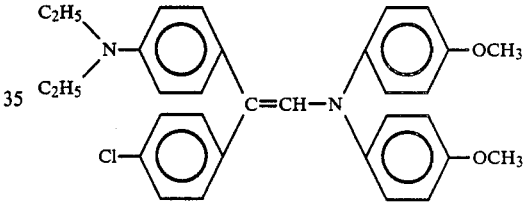
(4-6)

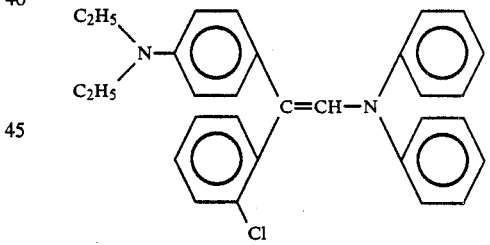
(4-7)

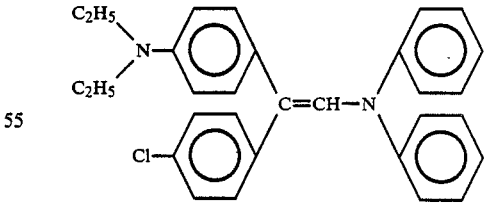
(4-8)

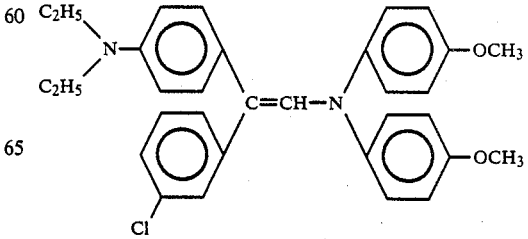
(4-9)

-continued

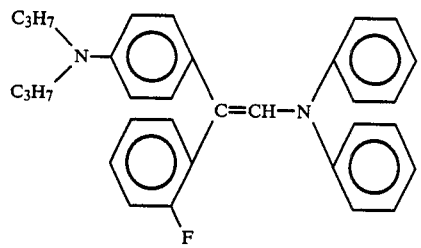  (4-10)

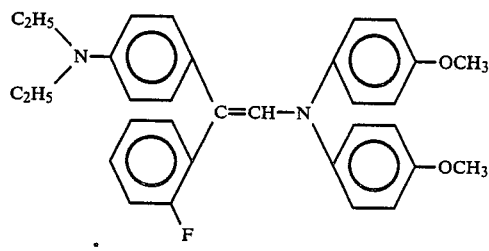  (4-11)

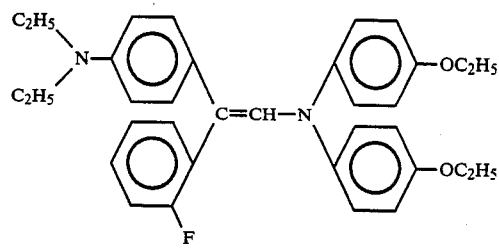  (4-12)

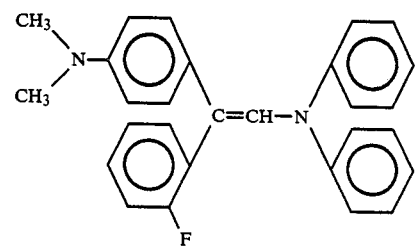  (4-13)

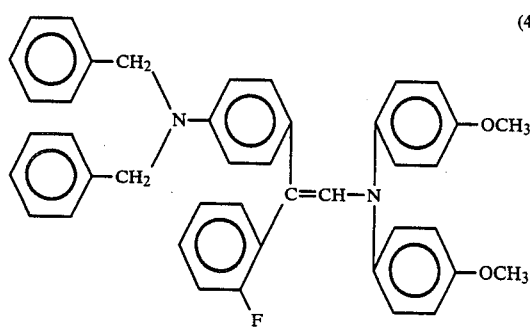  (4-14)

Still other enamine compounds used in the invention are those expressed by the following general formula

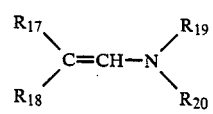  (I-5)

wherein $R_{17}$ and $R_{18}$ are independently hydrogen, halogen, alkyl group, or alkoxyaryl group, aralkyl group, alkyl group, di-substituted aminoaryl group, alkylaryl group, halogenized aryl group,

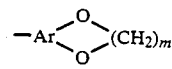

(Ar is an aryl group and m is 1 or 2), heterocyclic group or condensed polycyclic group, each of which may have one or more other substituents, providing that at least one of $R_{17}$ and $R_{18}$ are an condensed polycyclic group; and $R_{19}$ and $R_{20}$ are independently hydrogen, alkyl group, or phenyl group, alkoxyaryl group or aralkyl group, each of which may have one or more substituents excepting alkyl and/or di-substituted amino group, except that both the $R_{19}$ and $R_{20}$ are not hydrogen. $R_{19}$ and/or $R_{20}$ is most preferably a phenyl group or alkoxyphenyl group.

The typical preferred enamine compounds, expressed by (I-5), include those having the following structural formulas.

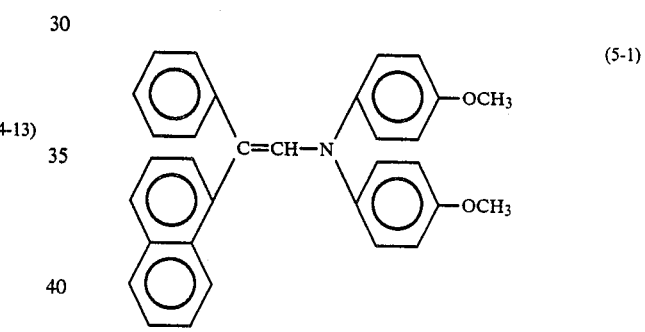  (5-1)

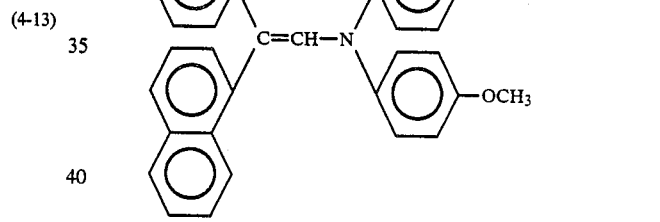  (5-2)

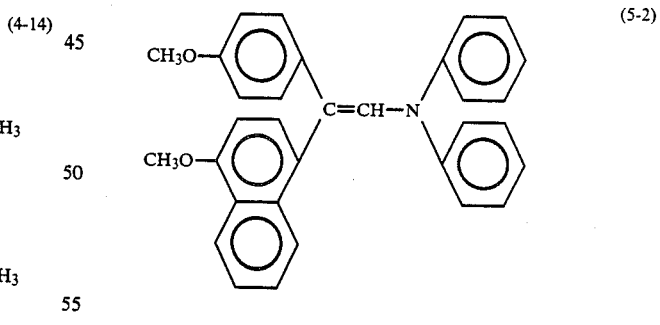  (5-3)

-continued
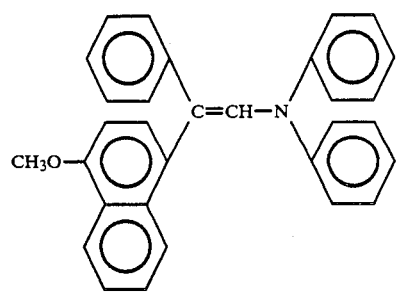 (5-4)
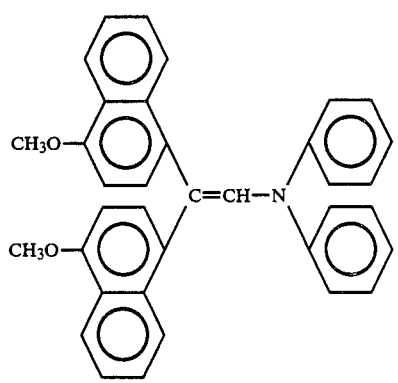 (5-5)
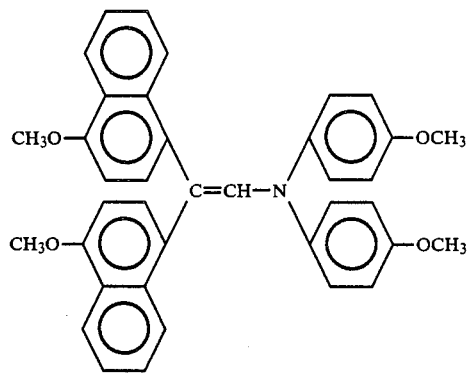 (5-6)
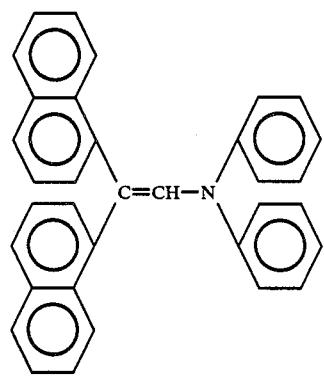 (5-7)
-continued
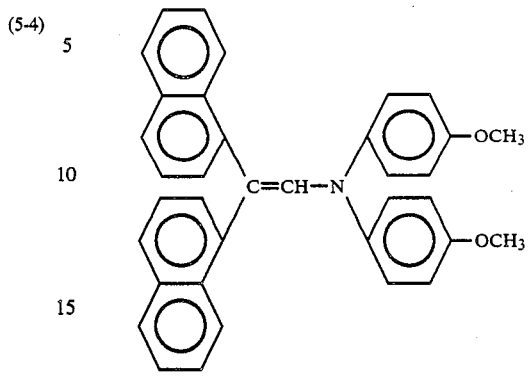 (5-8)
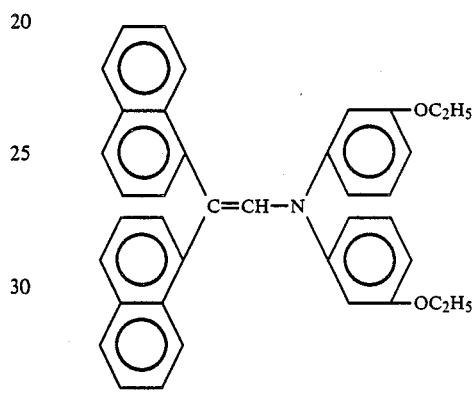 (5-9)
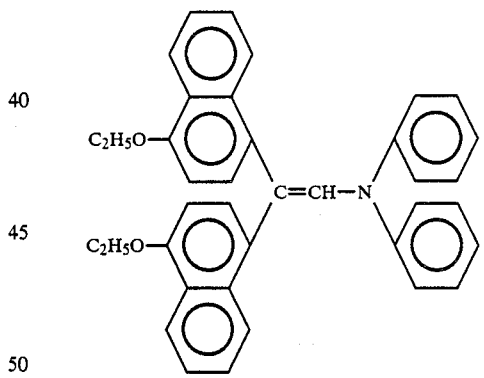 (5-10)
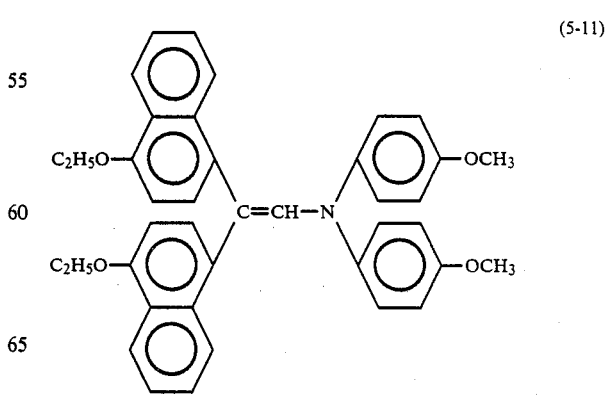 (5-11)

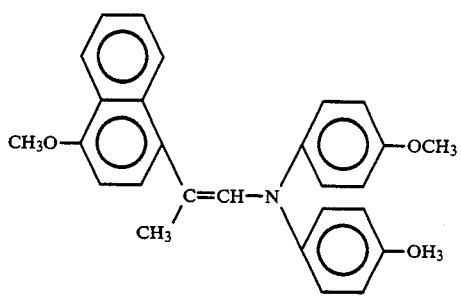
(5-12)

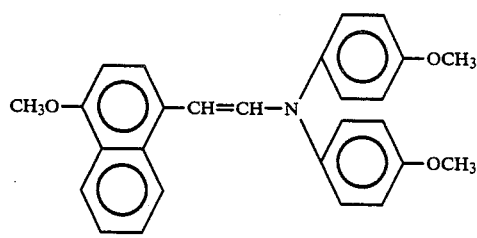
(5-13)

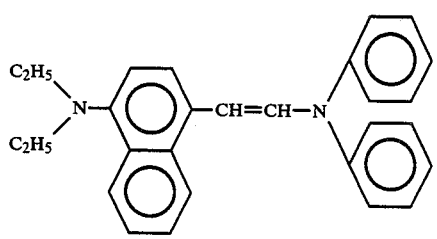
(5-14)

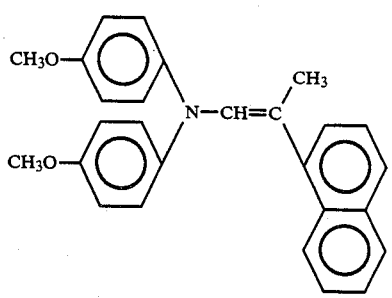
(5-15)

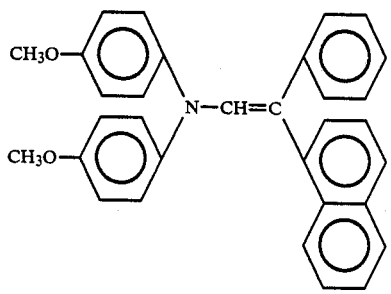
(5-16)

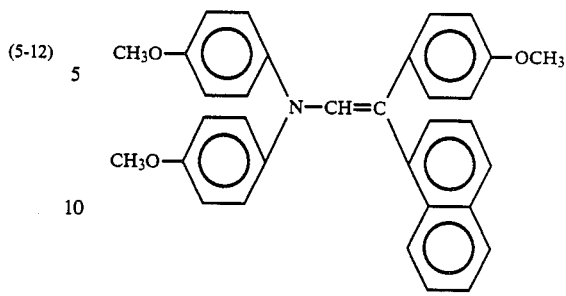
(5-17)

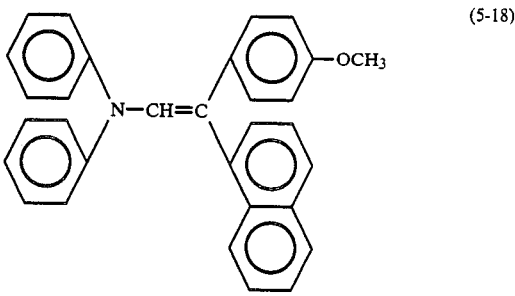
(5-18)

Still other enamine compounds used in the invention are those expressed by the following general formula:

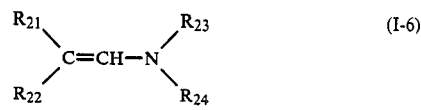
(I-6)

wherein $R_{21}$ and $R_{22}$ are independently hydrogen, halogen, alkyl group, or alkoxyaryl group, aralkyl group, alkyl group, di-substituted aminoaryl group, alkylaryl group, halogenized aryl group,

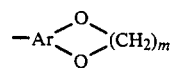

(Ar is an aryl group and m is 1 or 2), heterocyclic group or condensed polycyclic group, each of which may have one or more other substituents, providing that at least one of $R_{21}$ and $R_{22}$ are $C_1$–$C_4$ alkyl group; and $R_{23}$ and $R_{24}$ are independently hydrogen, alkyl group, or phenyl group, alkoxyaryl group or aralkyl group, each of which may have one or more substituents excepting alkyl and/or di-substituted amino group, except that both the $R_{23}$ and $R_{24}$ are not hydrogen. $R_{23}$ and/or $R_{24}$ is most preferably phenyl group or alkoxyphenyl group.

The typical examples of an enamine compound according to the invention expressed by general formula (I-6) include those having the following structures.

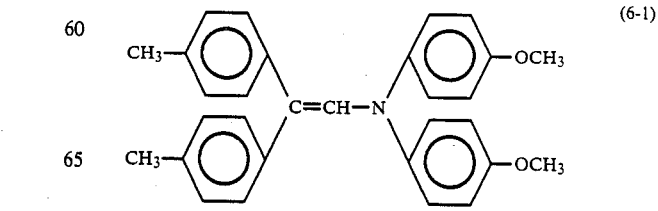
(6-1)

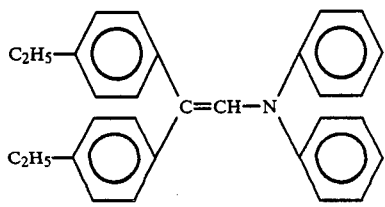
(6-2)

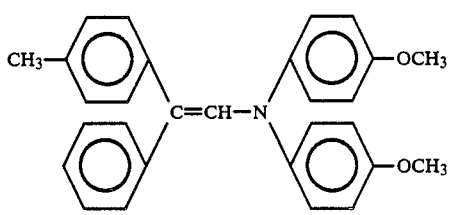
(6-3)

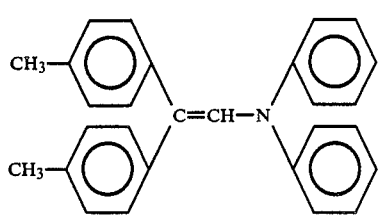
(6-4)

The enamine compounds expressed by the general formula (I) of the invention can be easily prepared with a known method.

For example, ordinary enamine compounds are synthesized with a method described in "Shin Jikken Kagaku Koza (lit., New Experimental Chemistry Course) 14-III, published by Maruzen Co., Ltd., pp 1417-1427.

The enamine compounds can be prepared by subjecting, for example, an amine compound expressed by the general formula (II),

(II)

wherein, X and Y are the same as those in (I) and an aldehyde compound expressed by the general formula (II),

(III)

wherein, T and W are the same as those in (I) to condensation via dehydration.

The condensation reaction is usually effected by removing the generated water through azeotropic distillation with a solvent such as benzene, toluene, xylene or the like, or by using a catalyst such as potassium carbonate, p-toluenesulfonic acid, acetic acid, Dowex 50 or Montmorillonite catalyst K10.

Desiccants used include molecular sieve, calcium oxide, calcium chloride, calcium carbonate and the like.

The constitutional examples of a photosensitive member using the enamine compound of the invention are schematically illustrated in FIGS. 1 through 5.

FIG. 1 illustrates a photosensitive member comprising a substrate 1, pro vided thereon, a photosensitive layer 4 containing a binder comprising a blend of a photoconductive material 3 and charge transporting material 2. As a charge transporting material, an enamine compound of the invention is used.

Figure 2:
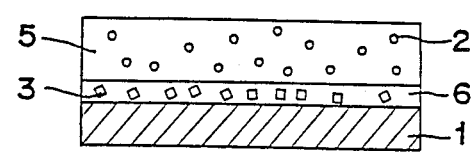

FIG. 2 illustrates a function-separating-type photosensitive member comprising, within a photosensitive layer, a charge generating layer 6 and a charge transporting member 5. The charge transporting layer 5 is provided on the surface of charge generating layer 6. An enamine compound of the invention is blended into the charge transporting layer 5.

Figure 3:
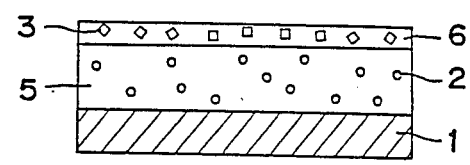

FIG. 3 illustrates a function-separating-type photosensitive member, similar to FIG. 2, comprising both a charge generating layer 6 and a charge transporting layer 5. In contrast to FIG. 2, however, the charge generating layer is provided on the surface of the charge transporting layer 5.

Figure 4:
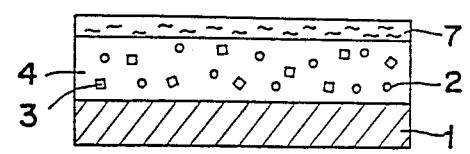

In FIG. 4, a surface protective layer 7 is additionally provided on the surface of the photosensitive member in FIG. 1, and a photosensitive layer 4 may be a function-separating-type layer comprising separately provided charge generating layer 6 and charge transporting layer 5.

Figure 5:
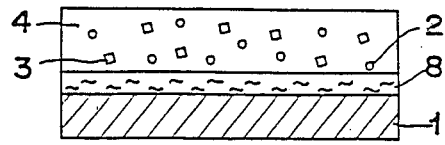

In FIG. 5, an intermediate layer 8 is provided between a substrate 1 and a photosensitive layer 4. Such an intermediate layer 8 can be provided in order to improve adhesion and coating properties, to protect the substrate, to improve the properties for injecting a charge from the substrate into the photoconductive layer. For an intermediate layer, a polyimide resin, polyester resin, polyvinylbutyral resin, casein and the like are advantageously used. A photosensitive member of this type may have a function separating type photosensitive layer.

The photosensitive member of the invention can be prepared by dissolving or dispersing an enamine compound expressed by the general formula (I) together with a binder into an optional appropriate solvent, into which a photoconductive material, electron attractive compound or sensitizing dye, and other pigments are further added in accordance with requirements; and the coating solution thus prepared is coated and dried on an electroconductive substrate so as to form a photosensitive layer having a thickness, normally 5-30 μm, preferably 6-20 μm.

More specifically, a functionally separate type photosensitive member having a constitution identical to that of FIG. 2 and comprising a charge generating layer and a charge transporting layer is prepared by forming a charge generating layer by vacuum-depositing a photoconductive material on an electroconductive substrate, or by coating and drying, on an electroconductive substrate, a coating solution prepared by dispersing a photoconductive material into an optional appropriate solvent or solvent with a binder resin having been dissolved, and; by coating and drying, on the charge generating layer, a solution prepared by dissolving an enamine compound and a binder into an optional appropriate solvent, in order to form a charge transporting layer. The thickness of such a charge generating layer is less than 4 μm, or preferably less than 2 μm. The thickness of such a charge transporting layer is 3-30 μm,, or preferably 5-20 μm. The advantageous content of enamine compound used in a charge transporting layer is 0.02-2 parts by weight, or preferably 0.03-1.3 parts by weight per part by weight binder. Additionally, other charge transporting material may also be used. A high-polymer charge transporting material, which itself can be used as a binder, can avoid the use of other binders. A photosensitive member may, like the similar member in FIG. 3, have a constitution involving an electroconductive substrate, provided thereon, a charge transporting layer on which a charge generating layer is further disposed.

A dispersion type photosensitive member comprising an electroconductive substrate, provided thereon, a photosensitive layer and having a constitution identical with that in FIG. 1 is prepared by dispersing particles of a photoconductive material into a solution into which an enamine compound and a resin have been dissolved, and coating and drying the solution on an electroconductive substrate. The thickness of the photosensitive layer is 3–30 μm, or preferably 5–20 μm. Too small an amount of photoconductive material results in poor sensitivity. Too large an amount of the material results in poor charging properties and smaller mechanical strength of a photosensitive layer. Accordingly, the amount of photoconductive material within a photosensitive layer is 0.01–2 parts by weight, or preferably 0.05–1 parts by weight per part by weight resin. The amount of enamine compound is 0.01–2 parts by weight, or preferably 0.02–1.2 parts by weight per part by weight resin. Additionally, an enamine compound can be co-used with a high-molecular photoconductive material such as polyvinyl carbazole or the like which itself is usable as a binder. Also, an enamine compound can be used together with another charge transporting material such as a hydrazone compound.

Those used as a photoconductive material of a photosensitive member of the invention are as follows: organic materials such as a bisazo pigment, triarylmethane dye, thiazine dye, oxazine dye, xanthene dye, cyanine coloring agent, styryl dye, pyrylium dye, azo pigment, quinachrydone dye, indigo pigment, perylene pigment, polycyclic quinone pigment, bisbenzimidazole pigment, indanthrone pigment, squalylium pigments and the like; and inorganic materials such as selenoium, selenium-tellurium, selenium-arsenic, cadmium sulfide, amorphous silicon and the like. Other than these materials, any material may be used for this purpose, as far as it can absorb light and generate a highly efficient charged carrier.

As a binder used in the invention, any of the following can be used: electrically insulative and known thermoplastic resins; thermosetting resins and photosetting type resins and photoconductive resins.

Though not limiting the scope of the invention, the examples of appropriate binder resin are as follows; thermoplastic binders such as saturated polyester resin, polyamide resin, acryl resin, ethylenevinyl acetate copolymer, ion-bridged olefin copolymer (ionomer), styrene-butadiene block copolymer, polyallylate, polycarbonate, vinyl chloride-vinyl acetate copolymer, cellulose ester, polyimide, styrene resin and the like; thermosetting binders such as epoxy resin, urethane resin, silicon resin, phenol resin, melamine resin, xylene resin, alkyd resin, thermosetting acryl resin and the like; photosetting resins; photoconductive resins such as poly-N-vinylcarbazole, polyvinylpyrene, polyvinylanthracene and the like; and other resins. These resins may be used independently, or combined with other resins.

Any of these electrically insulative resins has, when measured independently, a volume resistance greater than $1 \times 10^{12}$ Ω.cm. The more favorable resins are polyester resin, polycarbonate resin and acryl resin.

In addition to a binder, any of the following may be incorporated into a photosensitive member of the invention; plasticizers such as halogenated paraffin, polychlorinated biphenyl, dimethylnaphthalene, dibutylnaphthalate, O-terphenyl and the like; electron attractive sensitizers such as chloranil, tetracyanoethylene, 2,4,7-trinitro9-fluorenone, 5,6-dicyanobenzoquinone, tetracyanoquinodimethane, tetrachlorophthalic anhydride, 3,5-dinitrobenzoic acid and the like; sensitizers such as methyl violet, Rhodamine B, cyanine dye, pyrylium salt, thiapyrylium salt and the like.

A photosensitive member thus composed may have, as illustrated in FIGS. 4 and 5, an adhesive layer, intermediate layer 8 and surface protective layer 7, in accordance with specific requirements.

EXAMPLE 1

One part by weight disazo pigment represented by the general formula (A), below, one part by weight polyester resin (Vylon 200, manufactured by Toyobo Co., Ltd.) and 50 parts by weight tetrahydrofuran were poured into a ball mill pot where they were blended for 24 hours to prepare a photosensitive coating solution. The solution was coated and dried on an aluminum substrate to form a charge generating layer with a thickness 0.5μ.

General formula:

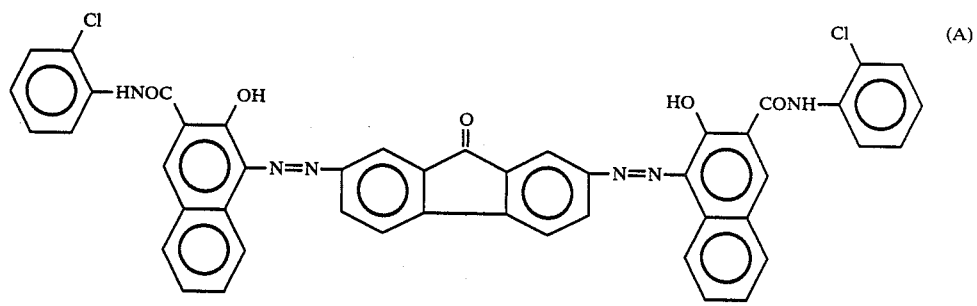

A coating solution prepared by dissolving ten parts by weight of the previously mentioned enamine compound (1-2) and ten parts by weight polycarbonate resin (Panlite K-1300, manufactured by Teijin Chemicals Ltd.) into 80 parts by weight tetrahydrofuran was coated and dried on the charge generating layer to form a charge transporting layer with a thickness 15μ. Thus, a photosensitive member was prepared.

Using a commercial elecrophotographic copier (EP360Z, manufactured by Minolta Camera Co., Ltd), the prepared photosensitive member was given a corona charge at −6.0 kV, then the initial potential $V_1(V)$, the exposure $E_{\frac{1}{2}}$ (lux. sec) required to reduce the initial potential to $\frac{1}{2}$, and the reduction rate $DDR_5$ (%) of the initial potential after the photosensitive member was left for five seconds in the dark were measured.

EXAMPLE 2

Two parts by weight trisazo pigment represented by the general formula (B), below, one part by weight polyester resin (Vylon 200, manufactured by Toyobo Co., Ltd.) and 100 parts by weight methyl ethyl ketone were poured into a ball mill pot, where they were blended for 24 hours to prepare a photosensitive coating solution. The solution was coated and dried on an aluminum substrate to form a charge generating layer with a thickness $1\mu$.

General formula:

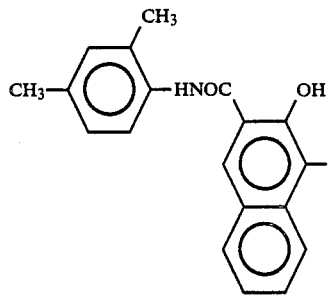 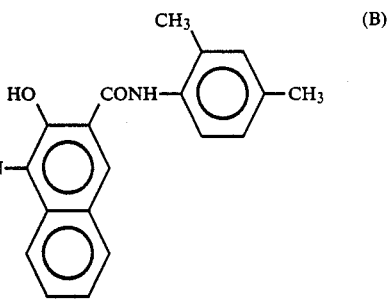

(B)

A coating solution prepared by dissolving ten parts by weight of the previously mentioned enamine compound (1-9) and ten parts by weight pollyallylate resin (U-100, manufactured by Unitika Ltd.) into 100 parts by weight chlorobenzene was coated and dried on the charge generating layer to form a charge transporting layer with a thickness of $15\mu$. Thus, a photosensitive member was prepared.

With the prepared photosensitive member, $V_0$, $E_{\frac{1}{2}}$ and $DDR_5$ were measured by a method identical to that in Example 1.

EXAMPLE 3

Two parts by weight squalenic acid pigment represented by the general formula (C), below, five parts by weight polyester resin (Vylon 200, manufactured by Toyobo Co., Ltd.) and 100 parts by weight methyl ethyl ketone were poured into a ball mill pot where they were blended for 24 hours to prepare a photosensitive coating solution. The solution was coated and dried on an aluminum substrate to form a charge generating layer with a thickness $1\mu$.

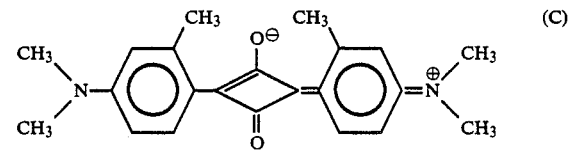

(C)

A coating solution, prepared by dissolving ten parts by weight enamine compound (1-5) and ten parts by weight polycarbonate resin (Panlite, manufactured by Teijin Chemicals Ltd.) into 80 parts by weight tetrahydrofuran, was coated and dried on the charge generating layer to form a charge transporting layer with a thickness of $15\mu$ when dried. Thus, a photosensitive member was prepared.

With the prepared photosensitive member, $V_0$, $E_{\frac{1}{2}}$ and $DDR_5$ were measured with a method identical to that in Example 1.

EXAMPLE 4

Fifty parts by weight copper phthalocyanine and 0.2 parts by weight tetranitro copper phthalocyanine were, with thorough stirring, dissolved into 500 parts by weight of 98% concentrated sulfuric acid, which was poured into 5000 parts by weight water so as to precipitate a blend of photoconductive material comprising copper phthalocyanine and tetranitro copper phthalocyanine. Then, the precipitate was filtered off, washed with water, and dried at 120° C. under reduced pressure.

Ten parts by weight of the obtained photoconductive composition was poured into a ball mill pot together with 22.5 parts by weight thermosetting acryl resin (Acrydic A 405, manufactured by Dainippon Ink & Chemicals, Inc.), 7.5 weight parts melamine resin (Super Beckamine J820, manufactured by Dainippon Ink & Chemical, Inc.), ten parts by weight of the previously mentioned enamine compound (1-8), and 100 parts by weight mixed solvent comprising equal amounts of methyl ethyl ketone and xylene. These were blended in a ball mill pot for 48 hours to prepare a photoconductive coating solution which was coated and dried on an aluminum substrate to form a photosensitive layer having a thickness of about $15\mu$. Thus a photosensitive member was prepared.

With the prepared photosensitive member, $V_0$, $E_{\frac{1}{2}}$ and $DDR_5$ were measured with the method identical to that in Example 1, except that the member was given a corona charge at +6 kV.

EXAMPLES 5-7

Photosensitive members J, K and L independently having the constitution identical to that in Example 4 were prepared by the method identical to that in Example 4, except that enamine compounds (1-12), (1-13) and (1-14) were used respectively in place of enamine compound (1-8) used in the Example 4.

With the prepared photosensitive members, $V_0$, $E_{\frac{1}{2}}$ and $DDR_5$ were measured with a method identical to that in Example 4.

The measured results of $V_0$, $E_{\frac{1}{2}}$ and $DDR_5$ of Examples 1-7 are shown in Table 1.

TABLE 1

|  | $V_0$ (V) | $E_{\frac{1}{2}}$ (lux.sec) | $DDR_5$ (%) |
|---|---|---|---|
| Example 1 | −660 | 2.6 | 4.0 |
| Example 2 | −660 | 2.8 | 5.0 |
| Example 3 | −640 | 3.2 | 6.5 |
| Example 4 | +650 | 1.5 | 12.0 |
| Example 5 | +650 | 1.6 | 11.5 |
| Example 6 | +640 | 1.6 | 13.0 |
| Example 7 | +650 | 1.7 | 11.0 |

As can be understood from Table 1, every photosensitive member of the invention, containing an enamine compound as a charge transporting material, has a surface potential more than 600 V, excellent sensitivity, smaller dark reduction rate, and excellent electrophotographic properties.

EXAMPLE 8

An electrophotographic photosensitive member was prepared in the same manner as Example 1, except that enamine compound (2-b 1) was used instead of enamine compound (1-2).

EXAMPLES 9-11

Photosensitive members were prepared in the same manner as in Example 1, except that enamine compounds (2-2), (2-3) and (2-6) were respectively used.

EXAMPLE 12

Two parts by weight trisazo pigment (B). and one part by weight polyester resin and 100 parts by weight methyl ethyl ketone were poured into a ball mill pot and blended for 24 hours to prepare a photosensitive coating solution. The solution was coated and dried on an aluminum substrate to form a charge generating layer having a thickness 1 μm. Ten parts by weight compound (2-10) was dissolved into a solvent, comprising ten parts by weight polyallylate resin (U-100, manufactured by Unitika Ltd.) and 100 parts by weight chlorobenzene, to prepare a coating solution which was coated on the charge generating layer to form a charge transporting layer having a thickness of μ. Thus, an electrophotographic photosensitive member was prepared.

EXAMPLES 13-14

Photosensitive members were prepared in the same manner as Example 12, except that enamine compounds (2-11) and (2-14) were respectively used.

EXAMPLE 15

An electrophotographic photosensitive member was prepared in the same manner as Example 3, except that enamine compound (2-9) was used instead of enamine compound (1-5).

EXAMPLE 16

An electrophotographic photosensitive member was prepared in the same manner as Example 4, except that enamine compound (2-17) was used instead of enamine compound (1-8).

EXAMPLES 17-19

Photosensitive members were prepared in the same manner as Example 4, except that enamine compounds (2-21), (2-22) and (2-23) were respectively used. To examine electrophotographic properties, the prepared electrophotographic photosensitive members were given a corona charge at −6.0 kV; for Examples 8-15, by using a commercial electrophotographic copier (EP360Z, manufactured by Minolta Camera Co., Ltd.). For Examples 16-19, the similar copier having been incorporated with a modification was used to give the members a corona charge at +6.0 kV in order to examine the similar properties.

With each member, an initial surface potential $V_0$ (V), exposure $E_{\frac{1}{2}}$ (lux. sec) required to reduce the initial potential to half, and dark reduction rate $DDR_5$ (%) of the initial potential after the member was left for five seconds in the dark were measured. The measurement results are shown in Table 2.

TABLE 2

|  | $V_0$ (V) | $E_{\frac{1}{2}}$ (lux.sec) | $DDR_5$ (%) |
|---|---|---|---|
| Example 8 | −660 | 2.8 | 4.0 |
| Example 9 | −650 | 2.5 | 5.5 |
| Example 10 | −660 | 2.1 | 4.0 |
| Example 11 | −670 | 2.6 | 3.0 |
| Example 12 | −650 | 4.8 | 6.0 |
| Example 13 | −670 | 5.4 | 2.5 |
| Example 14 | −660 | 4.3 | 5.0 |
| Example 15 | −640 | 5.0 | 8.0 |
| Example 16 | +640 | 3.5 | 12.0 |
| Example 17 | +630 | 1.8 | 13.0 |
| Example 18 | +640 | 2.0 | 10.0 |
| Example 19 | +640 | 1.9 | 11.5 |

EXAMPLE 20

An electrophotographic photosensitive member was prepared in the same manner as Example 1, except that enamine compound (3-1) was used instead of enamine compound (1-2).

Using a commercial elecrophotographic copier (EP360Z, manufactured by Minolta Camera Co., Ltd), the obtained photosensitive member was given a corona charge at −6.0 kV, then, the initial potential V0(V), the exposure $E_{\frac{1}{2}}$ (lux. sec) required to reduce the initial potential to ½, and the reduction rate $DDR_5$ (%) of the initial potential after the photosensitive member was left for five seconds in the dark were measured.

EXAMPLES 21-22

Using a method identical to that in Example 1, photosensitive members independently having the same constitution as Example 1 were prepared by using enamine compounds (3-5) and (3-13) respectively in place of enamine compound (1-2) used in Example 1.

With each of the prepared photosensitive members, $V_0$, $E_{\frac{1}{2}}$ and $DDR_5$ were measured by a method identical to that in Example 1.

EXAMPLES 23-24

Using a method identical to that in Example 2, photosensitive members independently having the same constitution as Example 2 were prepared by using enamine compounds (3-14) and (3-15) respectively in place of enamine compound (1-9) used in Example 2.

With each of the prepared photosensitive members, $V_0$, $E_{\frac{1}{2}}$ and $DDR_5$ were measured by a method identical to that in Example 1.

EXAMPLE 25

An electrophotographic photosensitive member was prepared in the same manner as Example 3, except that enamine compound (3-16) was used instead of enamine compound (1-5).

With the prepared photosensitive member, $V_0$, $E_{\frac{1}{2}}$ and $DDR_5$ were measured by a method identical to that in Example 1.

EXAMPLES 26

Using a method identical to that in Example 4, photosensitive member independently having the same constitution as Example 4 was prepared by using enamine compound (3-17) in place of enamine compound (3-19) used in Example 4.

With the prepared photosensitive member, $V_0$, $E_{\frac{1}{2}}$ and $DDR_5$ were measured with a method identical to that in Example 1, except that the member was given corona charge at +6 kV.

The measuring results of $V_0$, $E_{\frac{1}{2}}$ amnd $DDR_5$ for photosensitive members of Examples 20-26 are shown in Table 3.

TABLE 3

|  | $V_0$ (V) | $E_{\frac{1}{2}}$ (lux.sec) | $DDR_5$ (%) |
|---|---|---|---|
| Example 20 | −650 | 2.6 | 7.0 |
| Example 21 | −660 | 2.0 | 6.0 |
| Example 22 | −670 | 2.1 | 6.0 |
| Example 23 | −670 | 2.5 | 6.5 |
| Example 24 | −660 | 2.3 | 6.0 |
| Example 25 | −650 | 4.5 | 7.5 |
| Example 26 | +650 | 1.8 | 10.5 |

As can be understood from Table 3, every photosensitive member of the invention has a stable surface potential of more than 600 V, and excellent charging properties as its dark reduction rate is small enough for the practical use of a photosensitive member. The table also shows that every photosensitive member of the invention has a high sensitivity.

EXAMPLE 27

An electrophotographic photosensitive member was prepared in the same manner as Example 1, except that enamine compound (4-3) was used instead of enamine compound (1-2).

Using a commercial elecrophotographic copier (EP360Z, manufactured by Minolta Camera Co., Ltd), the obtained photosensitive member was given a corona charge at −6.0 kV, then the initial potential V0(V), the exposure $E_{\frac{1}{2}}$ (lux. sec) required to reduce the initial potential to $\frac{1}{2}$, and the reduction rate $DDR_5$ (%) of the initial potential after the photosensitive member was left for five seconds in the dark were measured.

EXAMPLES 28-30

Using a method identical to that in Example 1, photosensitive members independently having the same constitution as Example 1 were prepared by using enamine compounds (4-4), (4-6) and (4-7) respectively in place of enamine compound (1-2) used in Example 1.

With each of the prepared photosensitive members, $V_0$, $E_{\frac{1}{2}}$ and $DDR_5$ were measured by a method identical to that in Example 1.

EXAMPLE 31

An electrophotographic photosensitive member was prepared in the same manner as Example 2, except that enamine compound (4-8) was used instead of enamine compound (1-9).

With each of the prepared photosensitive members, $V_0$, $E_{\frac{1}{2}}$ and $DDR_5$ were measured by a method identical to that in Example 1.

EXAMPLES 32-33

Using a method identical to that in Example 2, photosensitive members independently having the same constitution as Example 2 were prepared by using enamine compounds (4-11) and (4-12) respectively in place of enamine compound (1-9) used in Example 2.

With each of the prepared photosensitive members, $V_0$, $E_{\frac{1}{2}}$ and $DDR_5$ were measured by a method identical to that in Example 1.

EXAMPLE 34

An electrophotographic photosensitive member was prepared in the same manner as Example 3, except that enamine compound (4-13) was used instead of enamine compound (1-5).

With the prepared photosensitive members $V_0$, $E_{\frac{1}{2}}$ and $DDR_5$ were measured by a method identical to that in Example 1.

EXAMPLE 35

An electrophotographic photosensitive member was prepared in the same manner as Example 4, except that enamine compound (4-16) was used instead of enamine compound (1-8).

With the prepared photosensitive member, $V_0$, $E_{\frac{1}{2}}$ and $DDR_5$ were measured by a method identical to that in Example 1, except that the member was given corona charge at +6 kV.

The measuring results of Vo, $E_{\frac{1}{2}}$ and $DDR_5$ for photosensitive members of Examples 27-35 are shown in Table 4.

TABLE 4

|  | $V_0$ (V) | $E_{\frac{1}{2}}$ (lux.sec) | $DDR_5$ (%) |
|---|---|---|---|
| Example 27 | −640 | 3.0 | 7.5 |
| Example 28 | −650 | 3.5 | 6.5 |
| Example 29 | −660 | 2.7 | 6.0 |
| Example 30 | −650 | 3.2 | 5.0 |
| Example 31 | −660 | 4.5 | 7.0 |
| Example 32 | −660 | 3.5 | 6.0 |
| Example 33 | −660 | 3.3 | 7.0 |
| Example 34 | −670 | 4.2 | 5.0 |
| Example 35 | +640 | 2.5 | 10.5 |

As can be understood from Table 4, every photosensitive member of the invention containing enamine compound has, regardless of whether it is a function separating type or dispersion type, an in tial surface potential of more than 600 V and excellent charging properties as its dark reduction rate is small enough for the practical use of a photosensitive member. The table also shows that every photosensitive member of the invention has excellent electrophotographic properties, and, especially, that the exposure to reduce the initial surface potential to the half value is approximately 2-4 lux.sec, hence the stable sensitivity.

EXAMPLE 36

An electrophotographic photosensitive member was prepared in the same manner an Example 2, except that enamine compound (5-2) was used instead of enamine compound (1-9).

Using a commercial electrophotographic copier (EP450Z, manufacture by Minolta Camera Co., Ltd.), the prepared photosensitive member was given a corona charge at +6 KV, then the initial potential $V_0$ (V), the exposure $E_{\frac{1}{2}}$ (lux.sec) required to reduce the initial potential to ½, and the reduction rate DDR₅ (%) of the initial potential after the photosensitive member was left for five seconds in the dark were measured.

EXAMPLE 37

Using a method identical to that in Example 2, photosensitive member having the same constitution as Example 2 was prepared by using enamine compound (5-3) in place of enamine compound (1-9) used in Example 2.

With the prepared photosensitive member, $V_0$, $E_{\frac{1}{2}}$ and $DDR_5$ was measured by a method identical to that in Example 36.

EXAMPLE 38

One part by weight of blend of photoconductive material prepared in Example 36 and comprising copper phthalocynine and tetranitro copper phthalocyanine, one part by weight polyester resin (Vylon 200, Toyobo Co., Ltd.) and 100 parts by weight methyl ethyl ketone were poured into a ball mill pot, where they were blended for 24 hours to prepare a photosensitive coating solution. The solution was coated and dried on an aluminum substrate to form a charge generating layer having a thickness of 1μ.

A coating solution prepared by dissolving ten parts by weight of the previously mentioned enamine compound (5-4) and ten parts by weight polycarbonate resin (Panlite K-1300, manufactured by Teijin Chemicals Ltd.) into 100 parts by weight tetrahydrofuran was coated and dried on the charge generating layer to form a charge transporting layer with a thickness of 15μ. Thus, a photosensitive member was prepared.

With the prepared photosensitive member, $V_0$, $E_{\frac{1}{2}}$ and $DDR_5$ were measured by a method identical to that in Example 36, except that the member was given a corona charge at $-6$ kV.

EXAMPLE 39

Two parts by weight disazo pigment represented by the general formula (A), one part by weight polyester resin (Vylon 200, manufactured by Toyobo Co., Ltd.) and 100 parts by weight methyl ethyl ketone were poured into a ball mill pot where they were blended for 24 hours to prepare a photosensitive coating solution. The solution was coated and dried on an aluminum substrate to form a charge generating layer with a thickness of 1μ.

A coating solution prepared by dissolving ten parts by weight of the previously mentioned enamine compound (5-11) into solvent, comprising polyallylate resin (U-100, manufactured by Unichika Ltd.) and 100 parts by weight chlorobenzene, was coated and dried on the charge generating layer to form a charge transporting layer with a thickness of 15μ. Thus, a photosensitive member was prepared.

With the prepared photosensitive member, $V_0$, $D_{\frac{1}{2}}$ and $DDR_5$ as measured by a method identical to that in Example 36.

The measurement results of $V_0$, $E_{\frac{1}{2}}$ and $DDR_5$ for photosensitive members of Examples 36–39 are shown in Table 5.

TABLE 5

| | $V_0$ (V) | $E_{\frac{1}{2}}$ (lux.sec) | $DDR_5$ (%) |
|---|---|---|---|
| Example 36 | +640 | 2.6 | 9.5 |
| Example 37 | +630 | 2.1 | 12.0 |
| Example 38 | −650 | 2.5 | 7.5 |
| Example 39 | −660 | 2.0 | 6.0 |

As can be understood from Table 5, every photosensitive member of the invention has a stable $V_0$ of more than 600 V, and excellent charging properties as its dark reduction rate is small enough for the practical use of a photosensitive member. The table also shows that every photosensitive member of the invention has a smaller $E_{\frac{1}{2}}$, 1.6–2.6 lux.sec, and high sensitivity. Furthermore, using an electrophotographic copier (EP350Z, manufactured by Minolta Camera Co., Ltd.), copying operation was repeated by giving a positive charge to the photosensitive members, Examples 36. In 10,000 copying sequences, both the first and final sequences could provide a copied image having excellent gradation. Without any change in sensitivity, high-definition images were obtained throughout the 10,000 copying sequences. Thus, every photosensitive member of the invention has stable repeatability.

COMPARATIVE EXAMPLES 1-8

Photosensitive members were produced in the same manner as in Example 4 excepting that the following eight enamine compounds (a)–(h) were used instead of the enamine compounds (1-8).

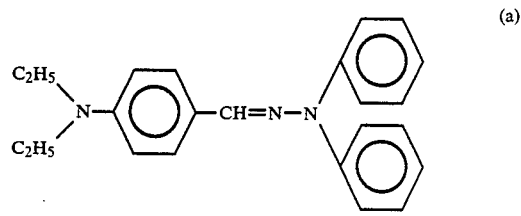
(a)

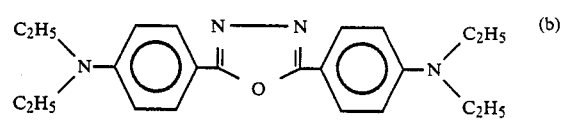
(b)

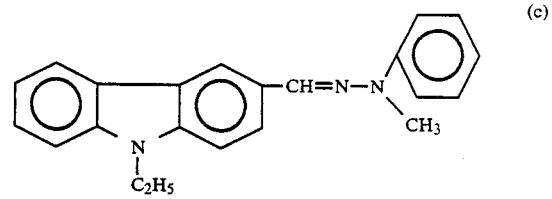
(c)

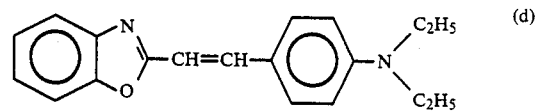
(d)

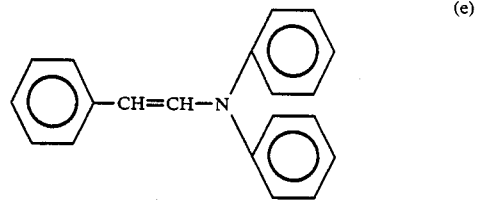
(e)

-continued

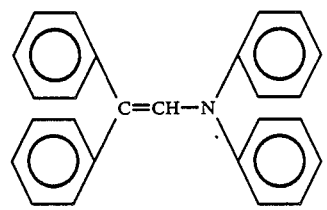 (f)

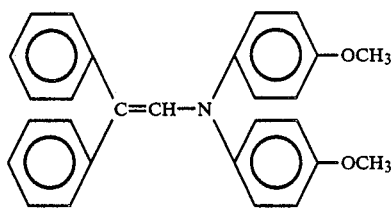 (g)

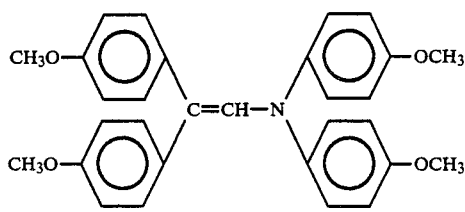 (h)

With the prepared photosensitive member, $V_0$, $E_{\frac{1}{2}}$, and $DDR_5$ were measured with the method identical to that in Example 4. The results are shown in Table 8.

TABLE 6

| Comparative Example | enamine compound | $V_0$ (V) | $E_{\frac{1}{2}}$ (lux.sec) | $DDR_5$ (%) |
|---|---|---|---|---|
| 1 | (a) | +640 | 2.8 | 18.0 |
| 2 | (b) | +660 | 32.7 | 6.5 |
| 3 | (c) | +650 | 3.1 | 15.0 |
| 4 | (d) | +660 | 5.8 | 13.0 |
| 5 | (e) | +650 | 39.4 | 5.0 |
| 6 | (f) | +660 | 8.9 | 11.0 |
| 7 | (g) | +660 | 6.3 | 12.5 |
| 8 | (h) | +630 | 2.4 | 20.0 |

On the surface of the photosensitive members of the Comparative Examples 2, 4 and 8, the crystals of the used enamine compounds were separated, and many white spots were observed on the printed image.

What is claimed is:

1. A photosensitive member having a photosensitive layer containing a charge generator and at least one enamine compound represented by the general formula (I) as a charge transporting material:

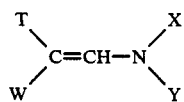 (I)

wherein T and W are independently hydrogen, halogen, alkyl group, or alkoxyaryl group, aralkyl group, di-substituted aminoaryl group, alkylaryl group, halogenated aryl group,

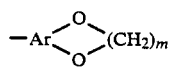

(Ar is aryl group and m is 1 or 2), heterocyclic group or condensed polycyclic group, each of which, except hydrogen and halogen, may have one or more other substituents, providing that at least one of T and W is an alkyl group, di-substituted aminoaryl group, alkylaryl group, halogenated aryl group,

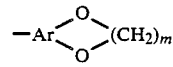

(Ar is an aryl group m is 1 or 2), heterocyclic group or condensed polycyclic group, each of which may have one or more other substituents, and X and Y are independently hydrogen, alkyl group, or phenyl group, alkoxyaryl group or aralkyl group, each of which, except hydrogen, may have one or more substituents excepting alkyl and/or di-substituted amino group, except that both the X and Y are not hydrogen.

2. The photosensitive member as claimed in claim 1 wherein the Ar group in the formula:

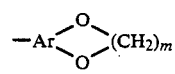

is a phenyl group or naphthyl group.

3. The photosensitive member as claimed in claim 1 wherein the phenyl group representedby X or Y is a phenyl group, alkoxyphenyl group which may have a $C_1$–$C_4$ alkyl group or halogenated phenyl group.

4. The photosensitive member as claimed in claim 1 wherein the di-substituted aminoaryl group represented by T and/or W is an aminophenyl group which may have a $C_1$–$C_4$ alkyl group, morpholinyl group, piperidyl group, piperazinyl group, 2,3-dihydropyridyl group or tetrahydroquinolyl group.

5. The photosensitive member as claimed in claim 1 wherein the halogenated phenyl group represented by T and/or W is a chlorophenyl or fluorophenyl group.

6. The photosensitive member as claimed in claim 1 wherein the heterocyclic group represented by T and/or W is a pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group.

7. The photosensitive member as claimed in claim 1 wherein the condensed polycyclic group represented by T and/or W is a naphthyl group, alkoxy group, di-substituted aminoaphthyl group or anthryl group.

8. The photosensitive member as claimed in claim 1 wherein the phenyl group represented by T and/or W is a phenyl group, $C_1$–$C_4$ alkoxy phenyl group or halogenated phenyl group.

9. The photosensitive member as claimed in claim 1 wherein the aralkyl group represented by T and/or W is benzyl group which may have one or more substituents.

10. The photosensitive member as claimed in claim 1 wherein the T and/or W is a halogenated phenyl group, and X and/or Y is a phenyl group or alkoxyphenyl group.

11. The photosensitive member as claimed in claim 1 wherein the T and/or W is a di-substituted aminoaryl group, and the X and/or Y is a phenyl group, alkoxyphenyl group or benzyl group.

12. The photosensitive member as claimed in claim 1 wherein the T and/or W is a heterocyclic group, and the X and/or Y is a phenyl group or alkoxyphenyl group.

13. The photosensitive member as claimed in claim 1 wherein the T and/or W is a group represented by the formula:

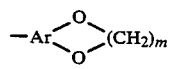

(m is 1 or 2), and X and/or W is a phenyl group, alkoxyphenyl group or benzyl group.

14. The photosensitive member as claimed in claim 1 wherein the T and/or W is a condensed polycyclic group, and the X and/or Y is a phenyl group or alkoxyphenyl group.

15. The photosensitive member as claimed in claim 1 wherein the enamine compound is expressed by the general formula;

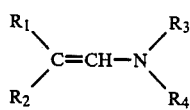

wherein, $R_1$ and $R_2$ are independently hydrogen, halogen, alkyl group, or alkoxyaryl group, aralkyl group, di-substituted aminoaryl group, alkylaryl group, halogenated aryl group,

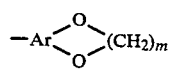

(Ar is an aryl group, and m is 1 or 2), heterocyclic group or condensed polycyclic group, each of which, except hydrogen and halogen, may have one or more other substituents, providing that at least one of $R_1$ and $R_2$ are an aminoaryl group which have a $C_1$-$C_4$ alkyl group, morpholinyl group, piperidyl group, piperazinyl group, 2,3-dihydropyridyl group or tetrahydroquinolyl group and aryl group is a phenyl, naphthyl or anthryl group; $R_3$ and $R_4$ are independently hydrogen, alkyl group, or phenyl group, alkoxyaryl group or aralkyl group, each of which, except hydrogen, may have one or more substituents excepting alkyl and/or di-substituted amino group, except that both the $R_3$ and $R_4$ are hot hydrogen.

16. The photosensitive member as claimed in claim 1 wherein the enamine compound is expressed by the general formula;

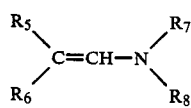

wherein $R_5$ and $R_6$ are independently hydrogen, halogen, alkyl group, or alkoxyaryl group, aralkyl group, alkyl group, di-substituted aminoaryl group, alkylaryl group, halogenated aryl group,

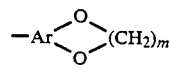

(Ar is an aryl group, and m is 1 or 2), heterocyclic group or condensed polycyclic group, each of which, except hydrogen, may have one or more other substituents, providing that at least one of $R_5$ and $R_6$ are an heterocyclic group selected from the group consisting of a pyridyl group, pyrrolyl group, purinyl group, carbazolyl group, indolyl group, thienyl group, furyl group, quinolyl group, phenothiazinyl group, indolinyl group, tetrahydroquinolyl group, thiophenyl group, 2,3-dihydrobenzofuryl group, dihydrobenzopyryl group, benzothiazolyl group, benzooxazolyl group, benzoimidazolyl group, thiazolyl group or dibenzofuryl group; and $R_7$ and $R_8$ are independently hydrogen, alkyl group, or phenyl group, alkoxyaryl group or aralkyl group, each of which, except hydrogen, may have one or more substituents excepting alkyl and/or di-substituted amino group, except that both the $R_7$ and $R_8$ are not hydrogen.

17. The photosensitive member as claimed in claim 1 wherein the enamine compound is expressed by the general formula;

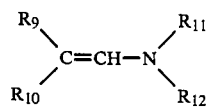

wherein $R_9$ and $R_{10}$ are are independently hydrogen, halogen, alkyl group, or alkoxyaryl group, aralkyl group, alkyl group, di-substituted aminoaryl group, alkylaryl group, halogenated aryl group,

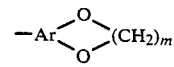

(Ar is an aryl group and m is 1 or 2), heterocyclic group or condensed polycyclic group, each of which, except hydrogen and halogen, may have one or more other substituents, providing that at least one of $R_5$ and $R_6$ are a group represented by the formula:

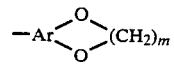

(m is 1 or 2, and Ar is an aryl group), and $R_{11}$ and $R_{12}$ are independently hydrogen, alkyl group, or phenyl group, alkoxyaryl group or aralkyl group, each of which, except hydrogen, may have one or more substituents excepting alkyl and/or di-substituted amino group, except that both the $R_{11}$ and $R_{12}$ are not hydrogen.

18. The photosensitive member as claimed in claim 1 wherein the enamine compound is expressed by the general formula:

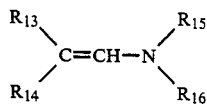

wherein $R_{13}$ and $R_{14}$ are independently hydrogen, halogen, alkyl group, or alkoxyaryl group, aralkyl group, alkyl group, di-substituted aminoaryl group, alkylaryl group, halogenated aryl group

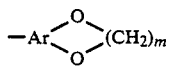

(Ar is an aryl group and m is 1 or 2), heterocyclic group or condensed polycyclic group, each of which, except hydrogen and halogen, may have one or more other substituents, providing that at least one of $R_{13}$ and $R_{14}$ are an halogenated aryl group; and $R_{15}$ and $R_{16}$ are independently hydrogen, alkyl group, or phenyl group, alkoxyaryl group or aralkyl group, each of which, except hydrogen, may have one or more substituents excepting alkyl and/or di-substituted amino group, except that both the $R_{15}$ and $R_{16}$ are not hydrogen.

19. The photosensitive member as claimed in claim 1 wherein the enamine compound is expressed by the general formula:

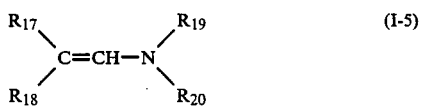

wherein $R_{17}$ and $R_{18}$ are independently hydrogen, halogen, alkyl group, or alkoxyaryl group, aralkyl group, alkyl group, di-substituted aminoaryl group, alkylaryl group, halogenated aryl group,

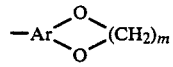

(Ar is an aryl group and m is 1 or 2), heterocyclic group or condensed polycyclic group, each of which, except hydrogen and halogen, may have one or more other substituents providing that at least one of $R_{17}$ and $R_{18}$ are an condensed polycyclic group; and $R_{19}$ and $R_{20}$ are independently hydrogen, alkyl group, or phenyl group, alkoxyaryl group or aralkyl group, each of which, except hydrogen, may have one or more substituents excepting alkyl and/or di-substituted amino group, except that both the $R_{19}$ and $R_{20}$ are not hydrogen.

20. The photosensitive member as claimed in claim 1 wherein the enamine compound is expressed by the general formula:

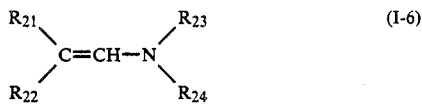

wherein $R_{21}$ and $R_{22}$ are independently hydrogen, halogen, alkyl group, or alkoxyaryl group, aralkyl group, alkyl group, di-substituted aminoaryl group, alkylaryl group, halogenated aryl group,

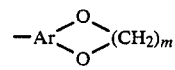

(Ar is an aryl group and m is 1 or 2), heterocyclic group or condensed polycyclic group, each of which, except hydrogen and halogen, may have one or more other substituents, providing that at least one of $R_{21}$ and $R_{22}$ are $C_1$–$C_4$ alkyl group; and $R_{23}$ and $R_{24}$ are independently hydrogen, alkyl group, or phenyl group, alkoxyaryl group or aralkyl group, each of which, except hydrogen, may have one or more substituents except alkyl and/or di-substituted amino group, excepting that both the $R_{23}$ and $R_{24}$ are not hydrogen.

* * * * *